United States Patent [19]
Arretz

[11] Patent Number: 5,919,971
[45] Date of Patent: Jul. 6, 1999

[54] PROCESS FOR THE SYNTHESIS OF 3-MERCAPTOPROPIONIC ACID ESTERS

[75] Inventor: Emmanuel Arretz, Pau, France

[73] Assignee: Elf Acquitaine Exploration Production France, Courbevoie, France

[21] Appl. No.: 08/975,662

[22] Filed: Nov. 21, 1997

[30] Foreign Application Priority Data

Nov. 22, 1996 [FR] France .................................. 96 14299

[51] Int. Cl.⁶ ................................................. C07C 319/04
[52] U.S. Cl. .......................................................... 560/152
[58] Field of Search ............................................ 560/152

[56] References Cited

U.S. PATENT DOCUMENTS

| | | |
|---|---|---|
| 3,346,516 | 10/1967 | Minton . |
| 5,008,432 | 4/1991 | Roberts . |
| 5,028,259 | 7/1991 | Lin et al. . |
| 5,340,380 | 8/1994 | Virnig . |

FOREIGN PATENT DOCUMENTS

| | | |
|---|---|---|
| 0 168 167 | 1/1986 | European Pat. Off. . |
| 0 198 680 A1 | 10/1986 | European Pat. Off. . |
| 0 198 680 B1 | 11/1990 | European Pat. Off. . |
| 3614065 | 11/1986 | Germany . |
| 56-147763 | 11/1981 | Japan . |
| 826837 | 1/1960 | United Kingdom . |

OTHER PUBLICATIONS

Copy of French Search Report dated Jul 23, 1997.
Fluka catalogue 1995/96, front page and p. 105.
Rich et al., Preparation of a New o–Nitrobenzyl Resin for Solid–Phase Synthesis of tert–Butyloxycarbonyl–Protected Peptide Acids, *Journal of the American Chemical Society* 97:6, pp. 1575–1579 (Mar. 19, 1975).

Iwakura et al., Polyurethane Sulfides Containing Cyclohexane Ring in the Polymer Chain, *Journal of Polymer Science: Part A*, vol. 2:881–893 (1964).

Mitchell et al., Preparation of Aminomethyl–Polystyrene Resin by Direct Amidomethylation, *Tetrahedron Letters No. 42*, Pergamon Press printed in Great Britain, pp. 3795–3798 (1976).

Voronkov et al., *Chem. Heterocycl. Compd.* (Engl. Transl.) 15, 1979, 1183–1185.

Eilingsfeld et al., Amidchloride und Carbamidchloride, *Angew. Chem.* 72:836–845 (1960).

Fujisawa et al., N,N,N',N'–Tetramethylchloroformamidinium Chloride as an Efficient Condensation Reagent for a Novel Esterification Applicable to the Macrolide Synthesis, *Chemistry Letters*:1891–1894 (1982).

Brederek et al., *Chem. Ber.* 94:2278–2295 (1961).

Ulrich et al., synthesis of Isocyanates and Carbodiimides, *Angew. Chem. Internat. Edit.* 5(No. 8):704–712 (1966).

Iijima et al., Polymer–Supported Bases.XI.Esterification and Alkylation in the Presence of Polymer–Supported Bicyclic Amidine or Guanidine Moieties, *J.M.S.—Pure Appl. Chem.* A29(3):249–261 (1992).

*Primary Examiner*—Robert Gerstl
*Attorney, Agent, or Firm*—Bell, Boyd & Lloyd

[57] ABSTRACT

This process for the synthesis of 3-mercaptopropionic acid esters by addition reaction of $H_2S$ to the corresponding acrylic acid ester is carried out in the presence of a solid-support functionalized with basic guanidine functional groups, on condition that these groups are free of hydrogen that is directly attached to a nitrogen atom.

11 Claims, 1 Drawing Sheet

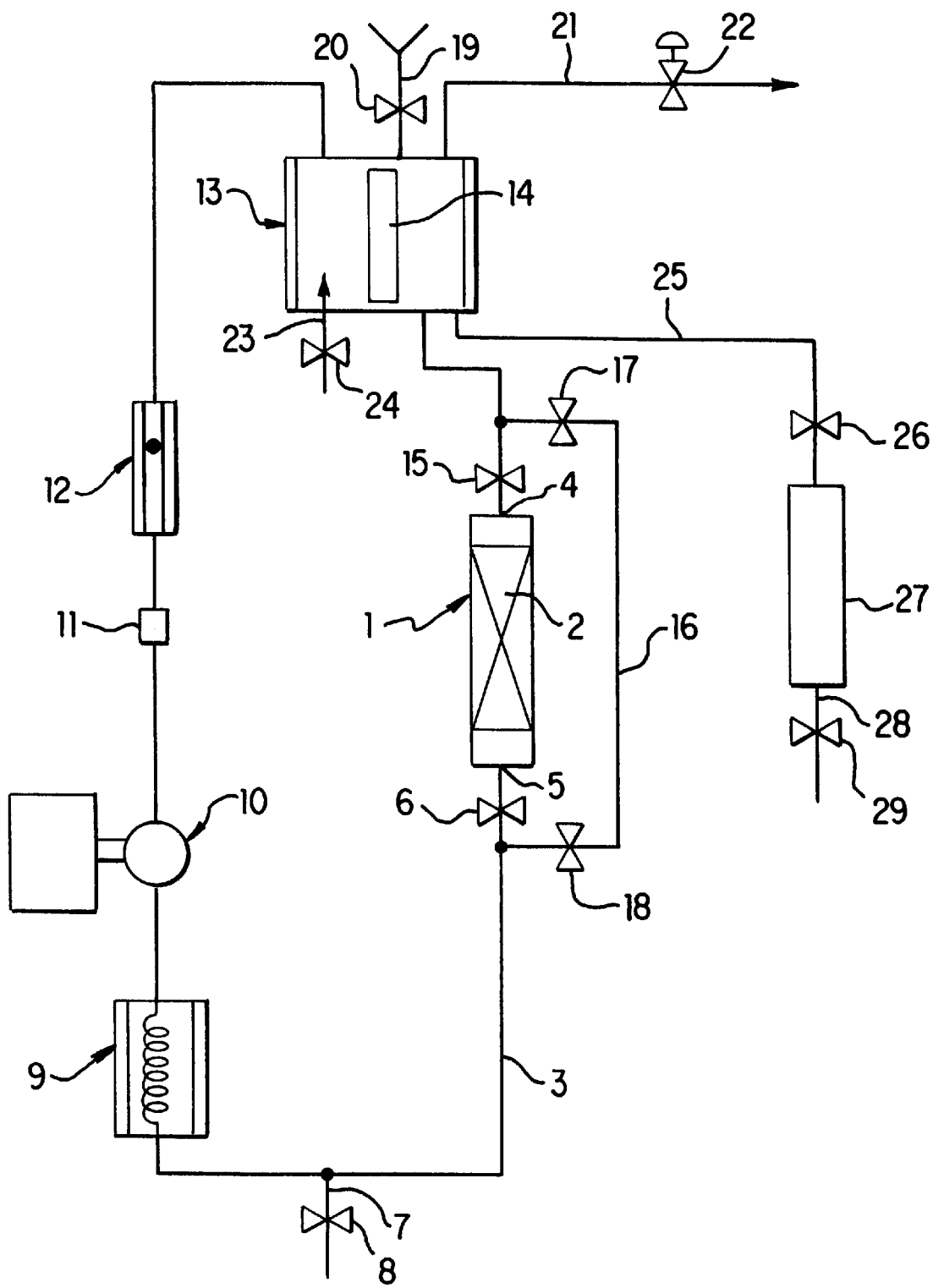

PROCESS FOR THE SYNTHESIS OF 3-MERCAPTOPROPIONIC ACID ESTERS

FIELD OF THE INVENTION

The present invention relates to the preparation of 3-mercaptopropionic acid (MPA) esters by addition of hydrogen sulphide to acrylic acid esters, according to reaction (1):

$$H_2S + CH_2=CH-COOR \rightarrow HS-CH_2-CH_2-COOR \quad (1)$$

The 3-mercaptopropionic acid ester formed may react with the acrylic acid ester present in the reaction medium to give the thio-3,3'-dipropionic acid ester according to reaction (2):

$$HS-CH_2-CH_2-COOR + CH_2=CH-COOR \rightarrow S(CH_2-CH_2-COOR)_2 \quad (2)$$

The group R above represents a straight or branched alkyl hydrocarbon group which may contain from 1 to 24 carbon atoms and may in particular be an alkylaryl group or a cyclohexyl group. The group R may be, for example, methyl, ethyl, propyl, butyl, pentyl, hexyl, heptyl, octyl, nonyl, decyl, undecyl or dodecyl.

BACKGROUND OF THE INVENTION

Processes for the synthesis of 3-mercaptopropionic acid esters are already known in the patent literature.

Thus, J56 147,763 describes such a process by addition of $H_2S$ to acrylic acid esters, using anion-exchange resins as catalysts, these resins having tertiary amines or quaternary ammonium hydroxides as functional groups.

U.S. Pat. No. 5,008,432 relates to the addition of $H_2S$ to unsaturated compounds whose olefinic double bond is conjugated with an electron-withdrawing group, for example acrylic acid esters.

This addition is carried out in the presence of a basic catalyst chosen from magnesium oxide and basic anion-exchange resins. These resins are chosen from those having tertiary amines or quaternary ammoniums as functional groups.

If an anion-exchange resin is used, the reaction pressure is generally from 3103 to 6895 kPa.

Example II describes the addition of $H_2S$ to methyl acrylate, without solvent, at a reaction pressure of 3102.75 kPa and at a temperature of 73° C., in the presence of Amberlyst A-21 resin (Rohm Haas). This resin possesses dimethylamino functional groups. The selectivity indicated is 97.3% with a conversion of 100%, the $H_2S$/methyl acrylate molar ratio being 6.3/1.

Example IV shows that the selectivities obtained are higher than the selectivities obtained at lower pressure (1931 kPa) according to J56 147,763.

Moreover, patent EP 0,168,167 describes the preparation of a silica or of an alumina functionalized with tetramethylguanidine.

The silica or the alumina is reacted with 2-[3-(triethoxysilyl)propyl]-1,1,3,3-tetramethylguanidine in order to graft this radical by formation of an —O—Si or —O—Al bond and removal of ethanol. The solid supports thus functionalized have been studied as basic catalysts in the transesterification.

DESCRIPTION OF THE INVENTION

The aim of the present invention is to find conditions for carrying out reaction (1) such that, while retaining a very high degree of conversion, the selectivity towards 3-mercaptopropionic acid ester is better than that of the prior art, in particular that which may be obtained from the technical teaching of document U.S. Pat. No. 5,008,432.

This aim is achieved by replacing the resins of the prior art by a solid support functionalized with guanidine groups, on condition that these groups are free of hydrogen that is directly attached to a nitrogen atom.

Thus, the present invention proposes a process for the synthesis of 3-mercaptopropionic acid esters by addition reaction of $H_2S$ to the corresponding acrylic acid ester in the presence of a solid support possessing basic functional groups, characterized in that the functional groups are guanidine groups, on condition that these groups are free of hydrogen that is directly attached to a nitrogen atom.

The solid support may be any support which is insoluble in the reaction medium comprising the acrylic ester, $H_2S$, the mercaptopropionic ester formed and, optionally, low amounts of the sulphide obtained by reaction (2).

The support may be, for example, silica, alumina or a polymeric resin.

In general, the insolubility of the resins is obtained by crosslinking of the polymer or polymers constituting the polymeric support.

More precisely, the present invention proposes a process for the synthesis of 3-mercaptopropionic acid esters by addition reaction of $H_2S$ to the corresponding acrylic acid ester in the presence of a solid support possessing basic functional groups, characterized in that these functional groups are chosen from:

1. a guanidine radical of general formula (C):

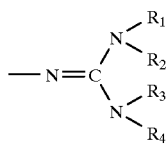

in which $R_1$, $R_2$, $R_3$ and $R_4$ are, independently of each other, hydrocarbon groups such as methyl, ethyl, propyl or butyl, the imine nitrogen being attached to the solid support by a series of chemical bonds, 2. a bicyclic guanidine radical of formula (D):

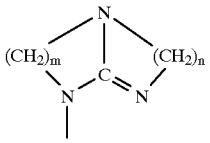

in which m and n are integers from 2 to 4, with the condition that n is less than or equal to m, this radical (D) being attached to the solid support by a chemical bond or a series of chemical bonds starting from the initially N—H nitrogen of the corresponding bicyclic guanidine.

The radical (D) is advantageously chosen from the radicals derived from the following guanidines: 1,5,7-triazabicyclo[4.3.0]non-6-ene (m=3, n=2), 1,5,7-triazabicyclo[4.4.0]dec-5-ene (m=3, n=3), 1,6,8-triazabicyclo[5.3.0]dec-7-ene (m=4, n=2), 1,4,6-triazabicyclo[3.3.0]oct-4-ene (m=2, n=2).

This process makes it possible to obtain, with an excellent degree of conversion of the acrylic ester, a better selectivity towards 3-mercaptopropionic acid ester than the processes of the prior art, with, in particular, a concomitant decrease in the content of sulphide diester in the reaction medium.

Thus, surprisingly, everything takes place as if the guanidine functional groups selectively increase the kinetics of reaction (1) relative to the kinetics of reaction (2).

The increase in selectivity towards 3-mercaptopropionic acid ester in the process according to the present invention is based below on the presentation of comparative examples including a quantitative calibration of chromatograms (see the experimental section).

The functionalized resin, based on polystyrene-divinylbenzene (PS-DVB), preferably has the general formula (I) below:

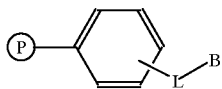
(I)

B being a group chosen from radicals of general formula (C) and (D), L being a linear organic radical which is as long as or longer than the methylene radical —($CH_2$)— and in particular the methylene radical,

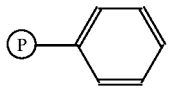

being the PS-DVB resin support.

Preferably, in the general formula (I):
the radical (C) is substituted with L, the latter then representing a —$CH_2$— radical, and $R_1$, $R_2$, $R_3$ and $R_4$ each representing a methyl group,
the radical (D) is substituted with L on the nitrogen which, in the related bicyclic compound, bears a hydrogen, with the condition that L then represents a radical —($CH_2$)$_p$—, p being an integer equal to 1 to 9.

Advantageously, the functionalized resin has the general formula (II):

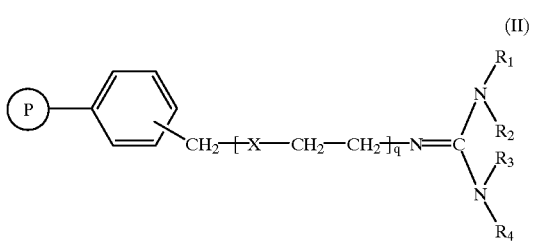
(II)

in which X represents an oxygen or sulphur atom, q is 1 or 2 and $R_1$, $R_2$, $R_3$ and $R_4$ are, independently of each other, chosen from methyl, ethyl, propyl and butyl groups.

Advantageously, in general formula (II), $R_1$, $R_2$, $R_3$ and $R_4$ each represent a methyl group and q is 1.

Preferably, resins containing bicyclic guanidine functions of general formula (D) are used in the process since they show greater chemical and thermal stability with respect to the reaction medium than the resins of general formula (C).

Preferably, the functionalized resin has the general formula (III):

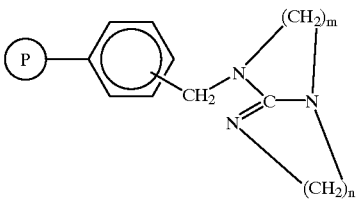
(III)

in which n is 2 or 3 and m is 2, 3 or 4, with the condition that n is less than or equal to m.

Preferably, the $H_2S$/acrylic acid ester molar ratio should be high in order to further promote reaction (1) relative to reaction (2). This molar ratio is usually from 3 to 10.

In order to increase this molar ratio in the liquid medium in contact with the functionalized resin acting as basic catalyst, it is preferred to subject the reaction medium to an $H_2S$ pressure greater than atmospheric pressure. Preferably, the reaction pressure is from 15 bar (1500 kPa) to 35 bar (3500 kPa).

Advantageously, the reaction is carried out at a temperature of from 15° C. to 80° C. Preferably, the temperature of the reaction medium ranges from 15° C. to 45° C.

Advantageously, the amount by weight of resin used relative to the amount by weight of acrylic acid ester used is from 1 to 100% and preferably from 10 to 70%.

The reaction may be carried out in a stirred or tubular reactor, according to a batchwise process, either by loading the reactants before they are reacted or by gradual addition of the acrylic acid ester after addition of the hydrogen sulphide, or alternatively by simultaneous addition of the reactants into the reactor, and, lastly, according to a continuous process with controlled addition of the reactants.

The functionalized resins of general formula (I) may be obtained or prepared in the following way:
1. The group B is a radical of general formula (C).

A process is known, from U.S. Pat. No. 5,340,380, which consists in substituting the chlorine of a chloromethylated polystyrene-divinylbenzene resin with a substituted or unsubstituted guanidine, which makes it possible to obtain resins of general formula (I.C):

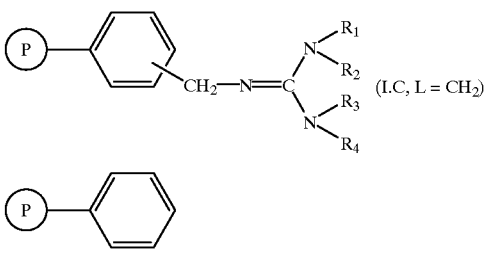
(I.C, L = $CH_2$)

representing the starting polystyrene-divinylbenzene solid support resin, it being possible for $R_1$, $R_2$, $R_3$ and $R_4$ each to be a hydrogen, an alkyl group or an aromatic group.

U.S. Pat. No. 3,346,516 also describes this reaction of a chloromethylated polystyrene-divinylbenzene resin with guanidine or tetramethylguanidine in the presence of a lower alcohol and a solvent for swelling the PS-DVB copolymer such as tetrahydrofuran, dioxane or diglyme.

In U.S. Pat. No. 5,028,259, the tetramethylguanidine is placed in contact with a chloromethylated polystyrene-divinylbenzene resin in a mixture of toluene and tetrahydrofuran.

In U.S. Pat. No. 5,340,380, guanidines are reacted with chloromethylated resins of this same type in the presence of sodium hydroxide in a solvent consisting of ethanol or water.

However, this technique for functionalizing a chloromethylated PS-DVB resin with a guanidine is very limited in practice as regards the production of resins of formula (I.C) whose guanidine radicals bear substituents $R_1$ to $R_4$ other than four methyls, insofar as only 1,1,3,3-tetramethylguanidine is currently commercially available.

Such resins (I.C) in which the groups $R_1$ to $R_4$ are all other than hydrogen may be obtained using tetrasubstituted ureas, which are often commercially available, under the following preparation conditions:

a) To begin with, a PS-DVB resin functionalized with primary amine groups is prepared, this resin having the general formula (I)

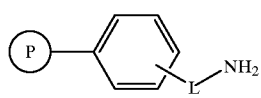

(A)

These resins may be obtained by various techniques:

1. It is possible, for example, to start with a resin of general formula (J):

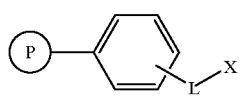

(J)

X being a leaving group, in particular halogen or tosylate obtained from a hydroxyl group —OH, and L representing in particular a radical —$(CH_2)_q$—, with q being an integer from 1 to 9, including 2.

Preferably, when L represents a single methylene, X is a chlorine atom. In this case, a method, described by D. H. Rich and S. K. Gurwara, J. Am. Chem. Soc., 1975, 97–1575–1579, consists in reacting a chloromethylated PS-DVB resin with an excess of ammonia. Another route is based on the production of phthalimidomethylated PS-DVB resin which is converted by hydrazinolysis into a resin containing primary amine functions. The two methods for gaining access to such phthalimidomethylated resins are described in the publication by A. R. Mitchell, S. B. H. Kent, B. W. Erickson and R. B. Merrifield, Tetrahedron Letters No. 42, 1976, 3795–3798. One consists in starting with a PS-DVB resin which, on reaction with N-(chloromethyl)phthalimide, is directly converted into phthalimidomethylated resin. The other method starts with a chloromethylated PS-DVB resin which is treated with potassium phthalimide to give the corresponding phthalimidomethylated resin.

A few PS-DVB resins containing primary amine functions of formula (A) in which L represents a methylene are commercially available.

Thus, the company PUROLITE proposes two macroporous resins, A-107 and A-109, whereas the company FLUKA has, in its 1995–1996 catalogue, two gel resins: the resin 08564 PS crosslinked with 2% DVB and containing 1.1 mmol of —$NH_2$ groups per gram of resin, and the resin 08566 PS crosslinked with 1% DVB and containing 0.6 mmol of —$NH_2$ per gram of resin.

The method with potassium phthalimide is also applicable to resins of formula (J) in the case where L is a linear organic radical longer than the methylene radical, in particular —$(CH_2)_r$—, with r being an integer greater than 1.

2. It is also possible to start with a PS-DVB resin of formula (J) in which L represents a methylene and X has the above meaning and preferably represents a chlorine atom. The Applicant has found that this chloromethylated resin may be reacted with an alkanolamine or a mercaptoalkylamine, in alkoxide or alkaline thiolate form, under the Williamson reaction conditions.

If ethanolamine is used, PS-DVB resins containing primary amine functions with —$CH_2$—O—$CH_2$—$CH_2$—$NH_2$ functional groups attached to the PS-DVB resin supports are obtained.

In a similar manner, starting with 2-aminoethanethiol hydrochloride, —$CH_2$—S—$CH_2$—$CH_2$—$NH_2$ functional groups are obtained.

If 2-(2-aminoethoxy)ethanol is used, PS-DVB resins containing primary amine functions with —$CH_2$—(O—$CH_2$—$CH_2)_2$—$NH_2$ functional groups are obtained.

Lastly, using 2-[(2-aminoethyl)thio]ethanethiol, —$CH_2$—(S—$CH_2$—$CH_2)_2$—$NH_2$ functional groups are obtained.

This starting mercaptoalkylamine may be prepared according to Iwakura et al., J. Polym. Sci. Pat A, 2, 1964, 881–883 or according to I. Voronkov, M. G. et al., Chem. Heterocycl. Compd. (Engl. Transl.) 15, 1979, 1183–1185.

The general conditions of the Williamson reaction are as follows:

The alkanolamine or the mercaptoalkylamine, diluted in anhydrous tetrahydrofuran (THF) or anhydrous N-methylpyrrolidone, is reacted with sodium hydride suspended in the same anhydrous solvent. After formation of the sodium alkoxide or of the sodium thiolate, the chloromethylated resin is introduced into the liquid reaction medium.

b) After obtaining the resin possessing primary amine groups of general formula (A), these primary amine groups are reacted with chloroformamidinium chloride (Vilsmeier salt) of general formula (H):

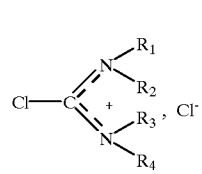

(H)

in which $R_1$, $R_2$, $R_3$ and $R_4$ are, independently of each other, chosen from methyl, ethyl, propyl and butyl groups, in order to obtain a PS-DVB resin functionalized with a guanidine group and of general formula (I.C):

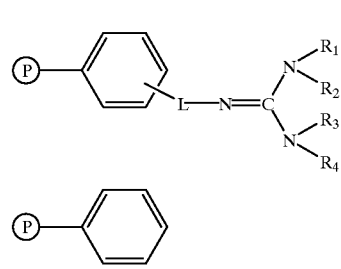

(I.C)

L and $R_1$ to $R_4$ having the same meanings as above.

The chloroformamidinium chlorides (H) are generally obtained from tetrasubstituted ureas by reaction with electrophilic compounds such as phosgene, thionyl chloride, oxalyl chloride or phosphorus oxychloride, according to methods described in the literature, in particular:

COCl$_2$ H. Eilingsfeld, M. Seefelder, Angew. Chem., 72, 1960, 836.

SOCl$_2$ H. Ulrich, A. A. R. Sayigh, Angew. Chem. Intern. Ed. Engl., 5, 1966, 704.

(COCl)$_2$ T. Fujisawa et al., Chem. Lett., 1982, 1891.

POCl$_3$ H. Bredereck, K. Bredereck, Chem. Ber., 94, 1961, 2278.

Generally, the process starts with stoichiometric amounts of tetrasubstituted ureas and electrophilic chloro compounds and is performed in the presence of a solvent such as carbon tetrachloride in the case of oxalyl chloride, or without solvents with phosgene or thionyl chloride, at a temperature generally of from 0° C. to 40° C., in anhydrous atmosphere in order to avoid any hydrolysis.

Advantageously, the tetrasubstituted ureas are chosen from tetramethylurea, tetraethylurea, tetra-n-propylurea and tetra-n-butylurea.

The chloroformamidinium chlorides (H) are generally placed in a solvent such as toluene or acetonitrile. Their reactions with resins containing primary amine functions (A) are carried out in the presence of a base, preferably in the presence of an excess of base.

If the base is triethylamine (TEA), the process is generally performed with a 10 to 50% molar excess of TEA relative to the chloroformamidinium chlorides (H). The latter are generally in a 10 to 100% molar excess relative to the number of moles of primary amine function, in order to convert all of the latter functions into guanidine functions.

2. In general formula (I), the group B is a radical of formula (D)

(a) To start with, a resin of general formula (J) is prepared as in point 1. a) above, L representing a radical —(CH$_2$)$_p$—, p being an integer equal to 1 to 9 and X being a chlorine or a bromine.

(b) The halogenated resin above is reacted with a bicyclic guanidine chosen in particular from 1,5,7-triazabicyclo[4.3.0]non-6-ene (m=3, n=2), 1,5,7-triazabicyclo[4.4.0]dec-5-ene (m=3, n=3), 1,6,8-triazabicyclo[5.3.0]dec-7-ene (m=4, n=2), 1,4,6-triazabicyclo 3.3.0]oct-4-ene (m=2, n=2).

The preparation of these bicyclic guanidines is described in patents GB 826,837 and EP 0,198,680.

The reaction is carried out in a similar manner to the process of M. Tomoi et al., J. M. S. Pure Appl. Chem. A29(3), 1992, 249–261, in particular page 251 ("Preparation of Polystyrene-Supported TBD").

A PS-DVB resin is thus obtained which is functionalized with a bicyclic guanidine group of general formula (I.D):

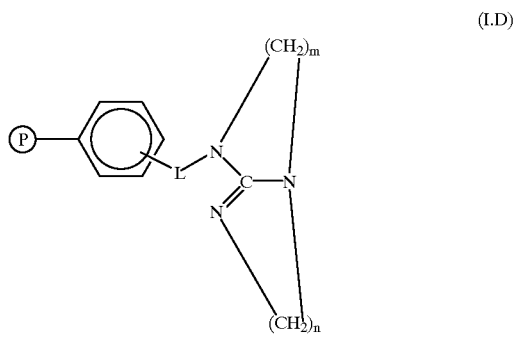

(I.D)

L representing a radical —(CH$_2$)$_p$— with p being an integer from 1 to 9.

The process of Tomoi et al., J. Macromol. Sci. Pure Appl. Chem. A29(3) 1992, 249–261, consists in reacting the lithium salt of TBD with a chloromethylated resin.

A simplified procedure has been studied in the context of the present invention in order to prepare larger amounts of resins containing TBD functions by reacting excess 1,5,7-triazabicyclo[4.4.0]dec-5-ene directly with chloromethylated PS-DVB resin in anhydrous THF as solvent.

The catalytic efficacy of the resins used in the present invention is improved when they are used dry.

EXAMPLES AND BACKGROUND DESCRIPTION OF THE DRAWING

The present invention will be better understood with the aid of the following experimental section, which comprises in particular a description of the apparatus used, the latter being represented diagrammatically in the single FIGURE attached.

EXPERIMENTAL SECTION

I. Preparation of polystyrene-divinylbenzene resins containing guanidine functions The chloromethylated PS-DVB base resin which is used is of macroporous type. It has the following characteristics:

Specific surface: 22.5 m$^2$/g of resin

Average pore diameter: 20 Å

Pore volume: 69%

Chloromethylated with a chlorine content of 19.32% by weight relative to the total weight. This resin thus contains 5.44 meq of Cl/g of resin.

I.1 Production of PS-DVB resins of formula (I.D) containing 1,5,7-triazabicyclo[4.4.0]dec-5-ene (TBD) functions with L=—CH$_2$—.

Procedure:

20 g of dry chloromethylated resin (5.44 meq of Cl/g of resin) are weighed out. The resin charge contains 0.109 mol of Cl. It is placed in contact, under a nitrogen atmosphere, with 30 g (0.216 mol) of TBD diluted in 285 g of THF which has been predried over molecular sieves. The reaction medium thus obtained is stirred mechanically for 48 hours at a temperature of 60° C. After cooling to 20° C., the resin is filtered off and is washed with 500 ml of water, and then with 250 ml of water at 60° C. It is then treated with 300 ml of aqueous 10% sodium hydroxide solution and washed with water until neutral. The resin is washed with methanol (300 ml) and then dried under vacuum at 60° C. to constant weight.

Elemental analysis was carried out on the resin thus obtained. For this resin, N=13.26% by weight, i.e. 3.15 mmol of TBD functions/g of resin. Resin referred to hereinbelow as: PS-DVB-TBD II Examples of the synthesis of methyl 3-mercaptopropionate II.1. General conditions The tests were carried out in apparatus which makes it possible to study under pressure the reaction for the formation of methyl 3-mercaptopropionate from methyl acrylate and hydrogen sulphide with various basic resins as catalysts.

Introduction of the reactants before starting the reaction makes it possible to carry out the reaction according to a batchwise process (the reaction progress is equivalent to the conditions of operating in a continuous piston regime).

The design of the apparatus (description of the apparatus: paragraph II.2) makes it possible to study the reaction in a stirred batchwise regime (closed reactor) using a tubular reactor (resin in a fixed bed) through which the liquid reaction medium circulates at a high flow rate by means of a pump on the circuit of a circulation loop which is connected to the two ends of the reactor.

This operating technique of stirred batch type makes it possible to study the reaction kinetics under conditions equivalent to conditions of operating in a continuous piston regime (open reactor), given that all of the reactants ($H_2S$ and methyl acrylate) are introduced into the apparatus before starting the reaction, the reactor being isolated (no contact with the resin) (operating procedure: paragraph II.3).

The reaction progress over time is monitored by taking samples which are analysed by gas chromatography in order to determine the conversion of the methyl acrylate and the corresponding selectivities towards methyl 3-mercaptopropionate and methyl thio-3,3'-dipropionate as a function of time.

II.2 Apparatus

As represented in the single figure, the stainless-steel apparatus is composed of the following elements:

a vertical tubular reactor 1 containing the charge of functionalized resin 2, a recirculation loop 3 emerging at the upper end 4 and at the lower end 5 of the reactor 1, this loop comprising pipes which successively connect, from the lower end 5, a closure valve 6, a branch pipe 7 equipped with a valve 8, a jacketed exchanger 9, a geared pump 10 (maximum flow rate 40 l/h), a temperature measurement point 11, a bead flow meter 12 and a jacketed cylindrical reservoir 13 fitted with a thick transparent glass inspection port 14. This reservoir 13 is connected to the upper end 4 of the reactor by a pipe passing via a closure valve 15. The reservoir 13 is placed above the reactor 1.

This circulation loop 3 itself includes a branch loop 16 equipped with 2 valves 17 and 18. This loop 16 makes it possible to isolate the reactor 1 from the circulation flow by means of the cooperation of the valves 6, 15, 17, 18.

The reservoir 13 is equipped at its upper part with a pipe 19 for introduction of methyl acrylate. This pipe 19 includes a valve 20. The reservoir 13 is also equipped with a pipe 21 equipped with a pressure valve 22. The pipe 21 is connected to a torch.

The reservoir 13 is equipped at its lower part with a pipe 23 equipped with a valve 24 and intended for the introduction of $H_2S$ under pressure into the reservoir.

The lower part of the reservoir is connected via a pipe 25 equipped with a valve 26 to a receiver 27. The latter is fitted in its lower part with a pipe 28 equipped with a valve 29. The pipe 28 allows samples to be collected during the reaction.

II.3 Operating procedure

The operations of loading the resin and introducing the methyl acrylate are carried out under a nitrogen atmosphere.

II.3.1 Preparation of the reaction mixtures

The reactor 1, containing the resin 2 (charges of about 8 g), is isolated from the rest of the apparatus by closing the valves 6 and 15. The methyl acrylate is introduced via the pipe 19 into the cylindrical reservoir 13 which is in direct communication with the recirculation loop. The apparatus is placed at a pressure of 3 bar of nitrogen. The cylindrical reservoir 13, in which the starting reaction mixture will be made up, is cooled by a circulation of oil at 5° C. (originating from a cryothermostat) which also passes through the outer jacket of the exchanger 9 of the recirculation loop. The circulation pump 10 is switched on and the liquid contained in the cylindrical reservoir circulates in the loop 3 and the loop 16, travelling from the reservoir 13 to the valve 17 before passing through the valve 18.

Hydrogen sulphide, obtained from a supply at a pressure of 16 bar, is injected via the pipe 23 into the reservoir 13 using a diffusor and dissolves in the cooled methyl acrylate.

At the end of the injection of $H_2S$, the pressure is 13 bar and the temperature of the liquid mixture (methyl acrylate+$H_2S$) is 15° C. The charge volume may be monitored by the inspection port 14.

II.3.2 Carrying out the tests

The cryothermostat is set to a value corresponding to the temperature at which the reaction should be carried out, and, while the oil is rising quickly to the set temperature, the circulating reaction mixture is introduced by opening the valves 15 and 6 and closing the valves 17 and 18 in the reactor 1 through which it circulates at a high flow rate (maximum: 40 l/h). The reaction temperature programmed for the test is maintained throughout the reaction. The pressure of the gas phase in the installation which is connected to the pressure valve 22 settles out between 16 bar and 28 bar, according to the test conditions.

During the test, at determined times, samples of the reaction medium are taken by means of the receiver 27 and are collected at atmospheric pressure and then analysed by gas chromatography. At the end of the test, the installation is depressurized and the final reaction product is recovered.

II.4. Analysis of the reaction products

Gas chromatography (GC) analyses are carried out using a Hewlett Packard 5890 FID chromatograph equipped with a 50 m capillary column containing a polydimethylsiloxane crosslinked phase (HP Ultra-1 origin).

II.5 Experimental tests

II.5.1 Operating conditions

The tests were carried out according to the operating procedure we used, which has been described in an earlier paragraph.

II.5.1.1 Resins

Comparative resin:

Amberlyst® A-21 resin (Rohm Haas) containing tertiary amine (dimethylamino) functions, given as an example in U.S. Pat. No. 5,008,432.

Resin of the invention:

Resin containing 1,5,7-triazabicyclo[4.4.0]dec-5-ene functions, prepared according to the procedure described above and referred to hereinbelow as: PS-DVB-TBD.

II.5.1.2 $H_2S$/methyl acrylate molar ratios:

4/1 or 6/1 or 8/1.

II.5.1.3 Temperatures:

15° C. or 30° C. or 45° C.

II.5.1.4 Operating pressures

The operating pressures depend upon the excess of $H_2S$ and on the reaction temperature.

The pressures exerted on the liquid of the reaction medium are such that the liquid is homogeneous (no degassing of $H_2S$).

Since the apparatus used cannot, for safety reasons, operate above a pressure of 29 bar, it was not possible to carry out a test at a temperature of 45° C. with an $H_2S$/methyl acrylate molar ratio equal to 8/1 since the operating pressure for this test would need to exceed 29 bar.

II.5.1.5 Monitoring of the reaction

Samples of the reaction medium liquid are taken at determined times and chromatographic analysis of these samples makes it possible to monitor the reaction progress and to determine the conversion of the methyl acrylate (MA) as a function of time as well as the corresponding selectivities towards methyl 3-mercaptopropionate (MMP).

Given the low amounts of resins used (8 g charges) relative to the amount of MA used, which is identical for each test (172 g, 2 mol), the reaction rates are relatively slow, and after 6 hours the conversions of the MA are not complete.

For the tests carried out at 30° C. or at 45° C., the reaction is continued for a further ½ hour and the apparatus is then emptied after it has been placed at atmospheric pressure. The crude reaction products are analysed by GC. The total reaction time is 6.5 hours.

Methyl acrylate: 172 g

Results: Table II

It is noted that the selectivity towards MMP is higher than that obtained above and that this selectivity virtually does not decrease when the reaction temperature increases.

TABLE I

| Test No. | $H_2S$/MA | Temp. ° C. | Pressure Bar | 2 hours | | 4 hours | | 6 hours | | 7 hours | | Crude reaction product | |
|---|---|---|---|---|---|---|---|---|---|---|---|---|---|
| | | | | Conv. MA (%) | Sel. MMP (%) | Conv. MA (%) | Sel. MMP (%) | Conv. MA (%) | Sel. MMP (%) | Conv. MA (%) | Sel. MMP (%) | Conv. MA (%) | Sel. MMP (%) |
| 1* | 4/1 | 15 | 16 | 58.6 | 93.4 | 83.6 | 91.6 | 94.5 | 91.4 | 97.9 | 91.0 | 98.5 | 90.9 |
| 2* | 4/1 | 30 | 20 | 78.8 | 89.9 | 93.4 | 89.6 | 97.6 | 89.6 | — | — | 98.9 | 89.5 |
| 3* | 4/1 | 45 | 28 | 85.7 | 88.7 | 95.5 | 88.6 | 98.3 | 88.5 | — | — | 98.3 | 88.5 |
| 4* | 6/1 | 15 | 17 | 51.9 | 95.4 | 71.1 | 95.2 | 88.8 | 95.1 | 95.5 | 95.0 | 98.4 | 94.9 |
| 5* | 6/1 | 30 | 22 | 74.4 | 94.0 | 91.7 | 93.6 | 96.9 | 93.4 | — | — | 98.8 | 93.3 |
| 6* | 6/1 | 45 | 28 | 79.5 | 92.8 | 92.9 | 92.5 | 97.2 | 92.4 | — | — | 98.5 | 92.3 |
| 7* | 8/1 | 15 | 20 | 41.0 | 94.9 | 62.9 | 94.8 | 80.9 | 94.6 | 89.0 | 94.6 | 95.8 | 94.6 |
| 8* | 8/1 | 30 | 24 | 59.5 | 94.7 | 82.7 | 94.5 | 93.8 | 94.4 | — | — | 98.1 | 94.1 |

*Comparative tests

TABLE II

| Test No. | $H_2S$/MA | Temp. ° C. | Pressure Bar | 2 hours | | 4 hours | | 6 hours | | 7 hours | | Crude reaction product | |
|---|---|---|---|---|---|---|---|---|---|---|---|---|---|
| | | | | Conv. MA (%) | Sel. MMP (%) | Conv. MA (%) | Sel. MMP (%) | Conv. MA (%) | Sel. MMP (%) | Conv. MA (%) | Sel. MMP (%) | Conv. MA (%) | Sel. MMP (%) |
| 9 | 4/1 | 15 | 16 | 64.6 | 94.2 | 85.7 | 94.1 | 95.4 | 94.0 | 98.8 | 93.9 | 99.4 | 93.6 |
| 10 | 4/1 | 30 | 20 | 89.8 | 93.8 | 96.4 | 93.6 | 98.5 | 93.5 | — | — | 99.3 | 93.5 |
| 11 | 4/1 | 45 | 28 | 92.9 | 93.6 | 97.1 | 93.3 | 98.9 | 93.2 | — | — | 99.5 | 93.1 |
| 12 | 6/1 | 15 | 17 | 54.2 | 96.1 | 68.9 | 96.0 | 87.5 | 95.9 | 94.9 | 95.8 | 98.1 | 95.8 |
| 13 | 6/1 | 30 | 22 | 82.0 | 95.9 | 92.8 | 95.5 | 97.1 | 95.5 | — | — | 99.0 | 95.5 |
| 14 | 6/1 | 45 | 28 | 83.3 | 95.4 | 93.8 | 95.2 | 98.1 | 95.1 | — | — | 98.9 | 95.0 |
| 15 | 8/1 | 15 | 20 | 40.7 | 96.9 | 61.7 | 96.8 | 80.3 | 96.8 | 89.1 | 96.8 | 97.8 | 96.8 |
| 16 | 8/1 | 30 | 24 | 74.7 | 97.1 | 90.0 | 96.8 | 96.1 | 96.7 | — | — | 98.6 | 96.7 |

For the tests carried out at 15° C., the reaction continues for a further one and a half hours with a sample taken at the end of the 7th hour, then the apparatus is emptied and the crude reaction product is analysed by GC. The total reaction time is 7.5 hours.

II.5.1.6 Presentation of the results

The comparative results obtained with the two resin charges above (Amberlyst® A-21 and PS-DVB-TBD) are represented in Tables I and II below.

These tables show the $H_2S$/MA molar ratio, the reaction temperature, the maximum reaction pressure, the sampling times with the corresponding values of the conversion of the methyl acrylate (MA) and of the selectivity towards methyl mercaptopropionate (MMP). The crude reaction product corresponds to the product collected at the end of the reaction.

II.5.1.6.1 Comparative tests with Amberlyst® A-21 resin
  Resin charge (dry): 8 g
  Methyl acrylate: 172 g
  Results: Table I It is noted that, for the same $H_2S$/MA molar ratio, the selectivity towards MMP decreases when the reaction temperature increases.

II.5.1.6.2 Tests according to the present invention with the resin PS-DVB-TBD
  Resin charge (dry): 8 g Although the invention has been described in conjunction with specific embodiments, it is evident that many alternatives and variations will be apparent to those skilled in the art in light of the foregoing description. Accordingly, the invention is intended to embrace all of the alternatives and variations that fall within the spirit and scope of the appended claims. The above references are hereby incorporated by reference.

I claim:

1. Process for the synthesis of 3-mercaptopropionic acid esters comprising synthesizing the esters by addition reaction of $H_2S$ to the corresponding acrylic acid ester in the presence of a solid support possessing basic functional groups selected from:
1. a guanidine radical of formula (C):

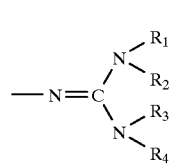

(C)

in which $R_1$, $R_2$, $R_3$, and $R_4$ are, independently of each other, hydrogen groups such as methyl, ethyl, propyl or butyl, the imine nitrogen being attached to the solid support by a series of chemical bonds, 2. a bicyclic guanidine radical of formula (D):

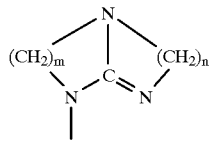
(D)

in which m and n are integers from 2 to 4, with the condition that n is less than or equal to m, this radical (D) being attached to the solid support by a chemical bond or a series of chemical bonds starting from the initially N—H nitrogen of the corresponding bicyclic guanidine.

2. Process according to claim 1, wherein the radical (D) is selected from the radicals derived from the following guanidines: 1,5,7-triazabicyclo [4.3.0] non-6-ene (m=3, n=2), 1,5,7-triazabicyclo [4.4.0] dec-5-ene (m=3, n=3), 1,6,8-triazabicyclo [5.3.0] dec-7-ene (m=4, n=2), 1,4,6-triazabicyclo [3.3.0] oct-4-ene (m=2, n=2).

3. Process according to claim 1, wherein the resin is based on polystyrenedivinylbenzene (PS-DVB) having the formula (I):

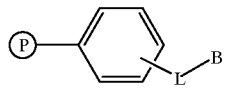
(I)

B being a group selected from radicals of formula (C) and (D), L being a linear organic radical which is as long as or longer than the methylene radical —(CH$_2$)— and optionally the methylene radical,

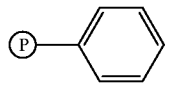

being the PS-DVB resin support.

4. Process according to claim 3, wherein
the radical (C) is substituted with L, the latter then representing a —CH$_2$— radical, and R$_1$, R$_2$, R$_3$ and R$_4$ each representing a methyl group,
the radical (D) is substituted with L on the nitrogen which, in the related bicyclic compound, bears a hydrogen,
with the condition that L then represents a radical —(CH$_2$)$_p$—, p being an integer from 1 to 9.

5. Process according to claim 3, wherein the polymeric resin has the formula (II):

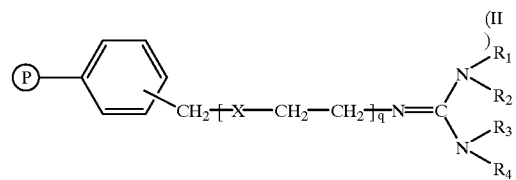
(II)

in which X represents an oxygen or sulphur atom, q is 1 or 2 and R$_1$, R$_2$, R$_3$ and R$_4$ are, independently of each other, selected from methyl, ethyl, propyl and butyl groups.

6. Process according to claim 5, wherein R$_1$, R$_2$, R$_3$ and R$_4$ each represent a methyl group and q is 1.

7. Process according to claim 1, wherein the functionalized resin has the formula (III):

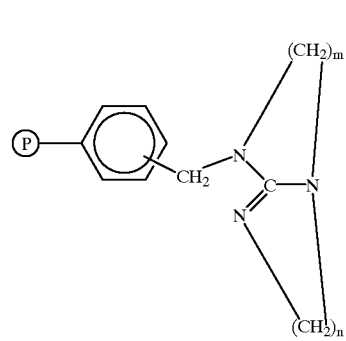
(III)

in which n is 2 or 3 and m is 2, 3 or 4, with the condition that n is less than or equal to m, this radical (D) being attached to the solid support by a series of chemical bonds.

8. Process according to claim 1, wherein the H$_2$S/acrylic acid ester molar ratio is from 3 to 10.

9. Process according to claim 1, wherein the reaction pressure is from 15 bar (1500 kPa) to 35 bar (3500 kPa).

10. Process according to claim 1, wherein the reaction is carried out at a temperature of from 15° C. to 80° C.

11. Process according to claim 10, wherein the reaction is carried out at a temperature of from 15° C. to 45° C.

* * * * *